US007947255B2

(12) United States Patent
Blakely et al.

(10) Patent No.: US 7,947,255 B2
(45) Date of Patent: May 24, 2011

(54) FLUORESCENT SUBSTRATES FOR NEUROTRANSMITTER TRANSPORTERS

(75) Inventors: Randy D. Blakely, Brentwood, TN (US); John N. Mason, Nashville, TN (US); Ian D. Tomlinson, Nashville, TN (US); Sandra J. Rosenthal, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 725 days.

(21) Appl. No.: 11/832,905

(22) Filed: Aug. 2, 2007

(65) Prior Publication Data

US 2008/0108102 A1 May 8, 2008

Related U.S. Application Data

(60) Provisional application No. 60/836,635, filed on Aug. 9, 2006.

(51) Int. Cl.
*A61K 49/00* (2006.01)
*G01N 33/52* (2006.01)

(52) U.S. Cl. ......................... 424/9.2; 435/7.21; 435/7.72

(58) Field of Classification Search ........................ None
See application file for complete search history.

(56) References Cited

U.S. PATENT DOCUMENTS

| 5,312,734 | A | 5/1994 | Uhl et al. ..................... 435/69.1 |
| 5,418,162 | A | 5/1995 | Blakely et al. ............. 435/252.3 |
| 5,424,185 | A | 6/1995 | Lam et al. ............................ 435/6 |
| 5,670,113 | A | 9/1997 | Akong et al. .................... 422/63 |
| 6,127,133 | A | 10/2000 | Akong et al. .................... 435/7.2 |
| 7,318,917 | B2 * | 1/2008 | Schwartz et al. .............. 424/9.2 |
| 2004/0115703 | A1 | 6/2004 | Schwartz et al. .............. 424/9.2 |

OTHER PUBLICATIONS

Iversen 2006 (British Journal of Pharmacology 147:S82-S88).*
Fromherz 1994 (Biochimica et Biophysica Acta—Biomembranes 1191(2):299-308).*
Bannon et al., "The human dopamine transporter gene: gene organization, transcriptional regulation, and potential involvement in neuropsychiatric disorders," *European Neuropsychopharmacology*, 11(6):449-55, 2001.
Blakely and DeFelice, "All aglow about presynaptic receptor regulation of neurotransmitter transporters," *Mol. Pharmacol.*, 71:1206-1208, 2007.
Bruns, "Serotonin transport in cultured leech neurons," *Methods Enzymol.*, 296:593-607, 1998.
Bulgarevich et al.,"Luminescence-spectral characteristics and conformational transformations in the electronically excited state of the dimethylaminophenyl derivatives of pyridine and pyridinium and pyrlium cations," *Khimiya Geterosiklicheskikh Soedinenii*, 5:625-630, 1992.
Coe et al., "Quadratic Optical Nonlinearities of N-Methyl and N-Aryl Pyridinium Salts," *Advanced Functional Materials*, 13(5):347-357, 2003.
Hadrich et al., "Synthesis and Characterization of Fluorescent Ligands for the Norepinephrine Transporter: Potential Neuroblastoma Imaging Agents," *J. Med. Chem.*, 42:3101-3108, 1999.
Ishikura et al., "A novel synthesis of 4-aryl- and 4-heteroarylpyridines via diethyl(4-pyridyl)borane," *Chem. Pharm. Bull.*, 33:4755-4763, 1985.
Lyapustina et al., "The twisted-intramolecular-charge-transfer-state-forming compound as a guest for cyclodextrins," *J. Photochem. Photobiol. A: Chem.*, 75(2):119-123, 1993.
Mason et al. "Real-time serotonin transporter function and antidepressant blockade monitored using a novel fluorescent pyrimidine derivative IDT307," *The Society for Neuroscience Conference*, Abstract # 531.5, Atlanta, GA, 2006.
Mason et al., "Monitoring biogenic amine transport with fluorescent substrates using confocal microscopy and microplate (FLEXstation) fluorimeters," *Molecular Devices Corp. FLIPR User Forum*, Seattle, WA, 2006.
Masson et al., "Neurotransmitter Transporters in the Central Nervous System," *Pharmacological Reviews*, 51:439-464, 1999.
Molecular Devices Corp. FLIPR User Forum in Seattle WA Sep. 16, 2006 and the Society for Neuroscience Conference in Atlanta, GA Oct. 2006.
Neumeister et al., "Association Between Serotonin Transporter Gene Promoter Polymorphism (5HTTLPR) and Behavioral Responses to Tryptophan Depletion in Healthy Women With and Without Family History of Depression," *Arch. Gen. Psychiatry*, 59(7):613-620, 2002.
Sora et al., Molecular mechanisms of cocaine reward: Combined dopamine and serotonin transporter knockouts eliminate cocaine place preference, *Proc. Natl. Acad. Sci. USA*, 98(9):5300-5305, 2001.
Tsai et al., "Association for Serotonin Transporter Gene Variable umber Tandem Repeat Polymorphism and Schizophrenic Disorders," *Neuropsychobiology*, 45(3):131-133, 2002.
Zauhar et al., "Synthesis of Dicyanomethyl and Nitro Submitted *p*-Polyphenyls and Their Salts," *Synthesis*, 6:703-706, 1995.
PCT International Search Report and Written Opinion, issues in International Application No. PCT/US2007/075461, dated Jan. 11, 2008.
Mason et al., "Real-time serotonin transporter function and antidepressant blockade monitored using a novel fluorescent pyrimidine derivative IDT307," *Soc. Neurosci. Abstr.*, 32:17, 2006.
Schwartz et al., "Binding and transport in norepinephrine transporters," *Journal of Biological Chemistry*, 278;9768-9777, 2003.

* cited by examiner

*Primary Examiner* — Daniel E Kolker
(74) *Attorney, Agent, or Firm* — Fulbright & Jaworski

(57) ABSTRACT

The invention is based on the finding that IDT307 and analogs thereof are fluorescent substrates transported by several neurotransmitter transporters. Provided are methods for the analysis of neurotransmitter transport and binding using IDT307 and its analogs. The invention also provides rapid methods for screening for modulators of neurotransmitter transport.

34 Claims, 8 Drawing Sheets

FLUORESCENT SUBSTRATES FOR NEUROTRANSMITTER TRANSPORTERS

This application claims priority to U.S. Application No. 60/836,635 filed on Aug. 9, 2006, the entire disclosure of which is specifically incorporated herein by reference in its entirety without disclaimer.

The government owns rights in the present invention pursuant to grant numbers R01EB03728-03 and RO1 DA07390 RB from the National Institutes of Health.

BACKGROUND OF THE INVENTION

1. Field of the Invention

The present invention relates generally to the fields of neurobiology and neurophysiology. More particularly, it concerns the methods and compositions for measuring the activity of neurotransmitter transporters. The invention also provides screening methods for identifying modulators of neurotransmitter transport.

2. Description of Related Art

Neurotransmitters mediate signal transduction in the nervous system and modulate the processing of responses to a variety of sensory and physiological stimuli. An important regulatory step in neurotransmission is the inactivation of a neurotransmitter following its release into the synaptic cleft. This is especially true for the biogenic amine and amino acid neurotransmitters. Inactivation of a neurotransmitter is typically mediated by uptake of the released neurotransmitter by neurotransmitter transporters that are located on the presynaptic neuron or in some cases on adjacent glial cells. Thus, neurotransmitter transporters are central to the processing of information in the nervous system and are associated with numerous neurological disorders.

For example, the neurotransmitter norepinephrine (also called noradrenalin) transduces signaling in the central nervous system that modulates attention, mood, arousal, learning, and memory (Aston-Jones et al., 1999; Coull et al., 1999; Skrebitsky and Chepkova, 1998; Hatfield and McGaugh, 1999). Norepinephrine (NE) transporters (NETs) attenuate neuronal signaling via rapid neurotransmitter clearance (Ressler and Nemeroff, 1999; Iversen et al., 1967; Axelrod and Kopin, 1969; Blakely et al., 1991). Norepinephrine transport is implicated in the pathology of major depression, post-traumatic stress disorder and attention deficit disorder (Ressler and Nemeroff, 1999; Southwick et al., 1999; Dow and Kline, 1997; Biederman and Spencer, 1999). Therapeutic agents that inhibit NET can elevate the concentration of norepinephrine in the brain and periphery (Axelrod and Kopin, 1969; Bonisch, 1984; Ramamoorthy et al., 1993; Galli et al., 1995; Corey et al., 1994; Fleckenstein et al., 1999). Noradrenergic signaling in the peripheral nervous system influences blood pressure and heart rate (Jones, 1991; Jacob et al., 1999; Hartzell, 1980), and NET inhibitors, such as cocaine and antidepressants, induce cardiac complications (Watanabe et al., 1981; Clarkson et al., 1993; Glassman et al., 1985).

Similarly other neurotransmitters such as epinephrine (E), dopamine (DA), serotonin (SE), and their respective transporters such as epinephrine transporters (ET), dopamine transporters (DAT), and the serotonin transporters (SERT), mediate diverse aspects of neuronal signaling and are involved in the pathology of numerous nervous system related disorders. Thus, neurotransmitter transporters are the targets of various therapeutic agents used in the treatment of neurological disorders including, depression, epilepsy, schizophrenia, Parkinson's disease, attention deficit disorders, eating and sleeping disorders as well as some neurodegenerative disorders. In some instances, treatment of these disorders is mediated by the use of pharmaceutical agents that are antagonists of a neurotransmitter transporter. Antagonists block uptake and prolong and/or enhance the action of the neurotransmitter. In other instances, treatment is mediated by use of pharmaceutical agents that are agonists of a neurotransmitter transporter. Agonists enhance uptake and rapidly clear the neurotransmitter, thereby terminating its actions. For example, imipramine, a blocker of SE and NE uptake, is used as an antidepressants; benztropine, an antagonist of dopamine uptake, temporarily alleviates the symptoms of Parkinson's disease; and blockers of γ-amino butyric acid (GABA) uptake are used in the treatment of epilepsy.

Despite the relevance of neurotransmitter transporters, the art is hindered by very limited methods that are used in studying neurotransmitter transporter functions such as kinetics, affinity, temporal and spatial aspects of transport, voltage dependence and other transport mechanics (Galli et al., 1995; Corey et al., 1994; DeFelice & Galli, 1998; Prasad and Amara, 2001). Methods used to study neurotransmitter transport typically involve the use of radiometric substrates to measure neurotransmitter accumulation. For example, $^3$H-labeled neurotransmitters are typically used to study transport of serotonin, epinephrine, norepinephrine, dopamine and the amino-acid transmitters (see for example U.S. Pat. No. 5,424, 185; Bonisch 1984; Bonisch and Harder, 1986; Hadrich et al., 1999). Although radiolabel techniques offer high specificity these approaches have significant limitations such as poor time and spatial resolution. In addition, none of these methods have the intrinsic capability to distinguish substrate binding from transport in the same assay. For example, non-permeating radiolabeled molecules that bind neurotransporters can characterize binding and count transporters, and permeating radiolabeled molecules can characterize transport, however, because of the poor time resolution of radiometric assays it is not possible to study binding and transport during the same experiment. Furthermore, these methods are not applicable for studying transport function in single mammalian cells. Although electrophysiology and amperometry alleviate some of these constraints, electrophysiology although rapid (in the millisecond time resolution) has poor substrate selectivity, while amperometry has the reverse characteristics (DeFelice and Galli, 1998; Galli et al., 1998).

Several other studies involved the use of fluorescent analogs of neurotransmitters for the study of neurotransmitter transporters. For example, Hadrich and colleagues generated fluorescent NE and nisoxetine analogs to image neuroblastomas (Hadrich et al., 1999) and Bruns (1998) used a autofluorescent analog of serotonin (5-HT), 5,7-dihydrotryptamine to identify a serotonin uptake current in leech neurons, however, these fluorescent compounds were also unable to distinguish substrate binding from transport. Additionally, fluorescent substrates based on neurotransmitter structures have the capability of activating cell surface receptors for the neurotransmitter during a transporter assay and causing indirect effects on transport activity, lessening their utility. Thus, new methods for the analysis of neurotransmitter transport function are highly desirable.

The present inventors previously reported the fluorescent substrate 4-(4-dimethylaminostyrl)-N-methylpyridinium (ASP$^+$) is transported by NET, DAT and SERT as well as methods to measure neurotransmitter transport mechanisms using ASP$^+$ and fluorescence microscopy. U.S. Publication No. 20040115703. ASP$^+$ was only minimally effective as a substrate for the serotonin transporter and exhibited transport by several other endogenous transporters that decrease signal to noise in transport assays, and also required the addition of fluorescence quenchers. Thus, additional substrates with distinct characteristics are needed to advance the understanding of neurotransmitter function.

SUMMARY OF THE INVENTION

The present invention overcomes the defects in the art and provides methods for the analysis of neurotransmitter transporters based on the use of fluorescent substrates. The invention also provides screening methods to identify agents that can modulate neurotransmitter transporters. In various embodiments, the fluorescent substrate may be advantageously used to measure neurotransmitter transporter activity without the use of a quencher, thus providing the additional benefit of avoiding any possible direct or indirect effects on a cell due to exposure to a quencher.

Thus, in accordance with the present invention, there is provided a method for measuring neurotransmitter transport in a cell comprising (a) providing a cell that expresses a neurotransmitter transporter; (b) exposing the cell or the extract to 4-(4-(dimethylamino)phenyl)-1-methylpyridinium iodide (IDT307); and (c) measuring the transport of IDT307, thereby measuring the transport of the neurotransmitter in the cell. Measuring transport may further comprise measuring the kinetics of the neurotransmitter transporter. Measuring transport may be performed in real time. Measuring transport may be by fluorescence microscopy or using a fluorescent plate reader. The time resolution of measuring transport may be 5 hours to 50 milliseconds.

It is contemplated that the screening methods will be automated to provide high-throughput screening of agents. For example, in some embodiments, the methods comprise the simultaneous screening of multiple agents with potential neurotransmitter transporter modulatory activities. This may be achieved by addition of reagents/components of the assay using robotic fluid delivery; the analysis of multiple samples in multi-well formats; using a fluorescent plate reader as well as other automation methods known in the art. Other examples of methods of automated equipment and assay procedures for membrane associated proteins such as ion channels are described in U.S. Pat. Nos. 6,127,133 and 5,670,113, the contents of which are incorporated by reference herein.

The cell may be a neuronal or glial cell, a blood platelet or lymphocyte, a placental cell or a trophoblast. The neurotransmitter transporter may be an endogenously expressed transporter or an exogenously expressed transporter. Recombinant DNA technology may be used to express any neurotransmitter transporter exogenously in a cell using methods of molecular biology as are known to one of skill in the art. The specification provides detailed description of methods used for exogenous expression infra. One of skill in the art would be well equipped to construct an expression vector that expresses nucleic acids encoding any neurotransmitter transporter using standard molecular biology techniques (see, for example, Maniatis et al., 1988 and Ausubel et al., 1994, both incorporated herein by reference). Furthermore, Galli et al. (1995), Ramamoorthy (1998), and U.S. Pat. Nos. 5,312,734, 5,418,162, & 5,424,185, all incorporated herein by reference, describe numerous nucleic acids, constructs and host cells used to express neurotransmitter transporters. The neurotransmitter transporter may be a monoamine neurotransmitter transporter, such as a norepinephrine transporter, a dopamine transporter or a serotonin transporter.

In another embodiment, there is provided a method of screening for agents that can modulate the activity of a neurotransmitter transporter comprising (a) providing a cell that expresses a neurotransmitter transporter; (b) exposing said cell to an agent that is a candidate neurotransmitter transporter modulator; (c) exposing the cell to 4-(4-(dimethylamino)phenyl)-1-methylpyridinium iodide (IDT307); (d) measuring the transport of IDT307; and (e) comparing the transport of IDT307 in said cell to the transport of IDT307 in a cell that has not been exposed to the agent, thereby determining if the agent is a modulator of activity of said neurotransmitter transporter. The cell may be a neuronal or glial cell, a blood platelet or lymphocyte, a placental cell, or a trophoblast.

The method may further comprise the use of a fluorescent plate reader to provide high-throughput screening of agents. The neurotransmitter transporter may be a norepinephrine transporter, an epinephrine transporter, a dopamine transporter or a serotonin transporter. The method may be an in vitro method or an in vivo methods, such as transgenic animals. It is contemplated that one may use animals such as mice or C. elegans as the genetics of these systems as well as methods for establishing transgenics are well known in these animals. Animals expressing certain types of neurotransmitter transporters can be provided with candidate modulatory agents and the transport of IDT307 or other fluorescent substrate can be imaged in vivo or in situ. General methods for in vivo imaging are described in Herrera and Banner (1990), and in Herrera et al., (1990), the contents of both are incorporated herein by reference. In situ methods for analysis are exemplified by the work by Ullrich and colleagues (Pietruck and Ullrich, 1995; Rohlicek and Ullrich, 1994, the contents of both are incorporated herein by reference). These methods may be suitably modified with the other teachings of the specification. The present invention contemplates the use of these methods in conjunction with the screening methods described herein. Measuring the transport of IDT307 may further comprise adding a quencher and measuring the polarization of light in the presence and absence of the agent.

Also provided are kits comprising (a) 4-(4-(dimethylamino)phenyl)-1-methylpyridinium iodide in a container; and (b) one or more neurotransmitter agonists or antagonists in one or more suitable containers.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
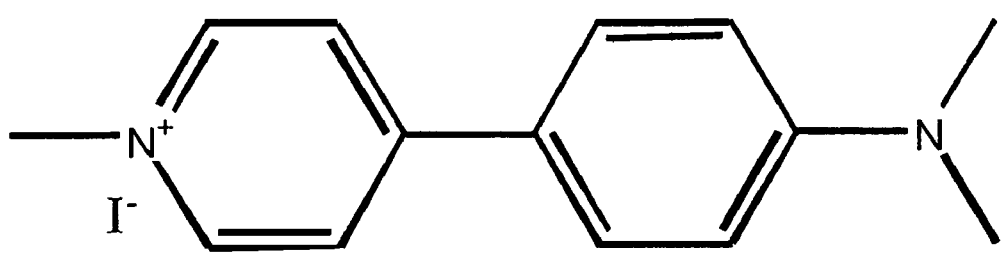
FIG. 1—Structure of 4-(4-(dimethylamino)phenyl)-1-methylpyridinium iodide (IDT307).
Figure 2:
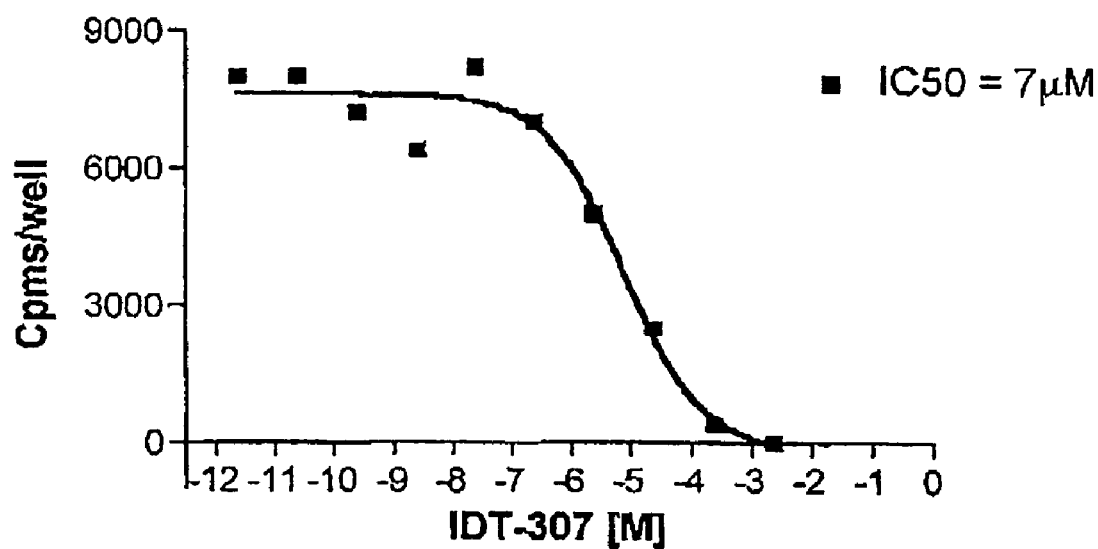
FIG. 2—[$^3$H]5-HT uptake inhibition by IDT307 of SERT. IDT307 competes for [$^3$H]5-HT uptake in LLC cells stably expressing the serotonin transporter. LLC cells stably expressing hSERT were incubated with [$^3$H]5-HT (30 nM) in the presence of increasing concentrations of IDT307 ($10^{-12}$ to $10^{-3}$) for 5 min at 37° C. Specific uptake was defined as total uptake minus uptake in the presence of the inhibitor paroxetine 1 μM.
Figure 3:
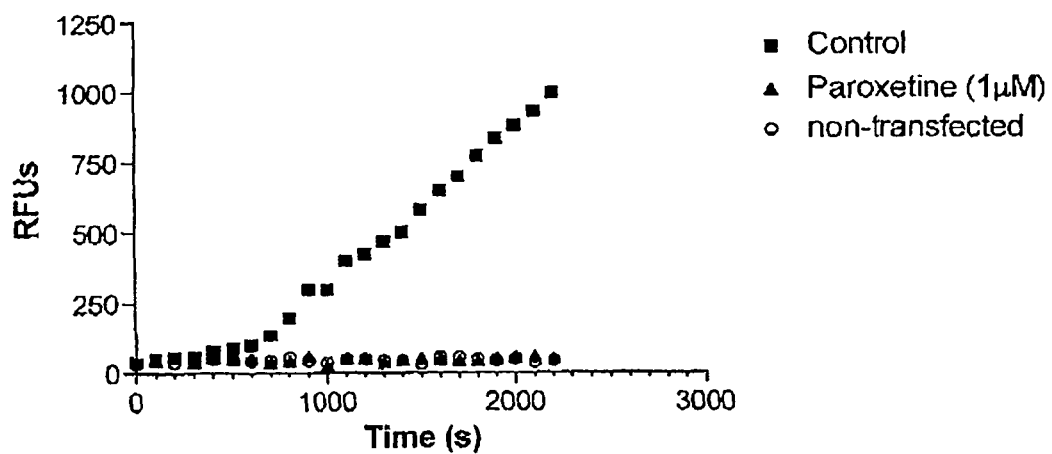
FIG. 3—IDT307 accumulation using a FlexStation™ fluorimeter. IDT307 accumulation using the FlexStation fluorimeter (excitation 440 nm/emission filter 595 nm). LLC non-transfected and hSERT expressing (control) cells were cultured in separate wells of a 96-well plate until confluent. The accumulation of IDT307 (10 μM) in these wells was then monitored in the presence and absence of paroxetine (1 μM) using the FlexStation.
Figure 4:
FIGS. 4A-D—IDT307 fluorescence with LLC-hSERT expressing cells. IDT307 fluorescence within LLC-hSERT expressing cells following a 40 min incubation with IDT307 (23 μM) in the presence or absence of paroxetine. After IDT307 accumulation cells were imaged using epifluorescence microscopy. Camera exposure time=1 sec.
Figure 5:
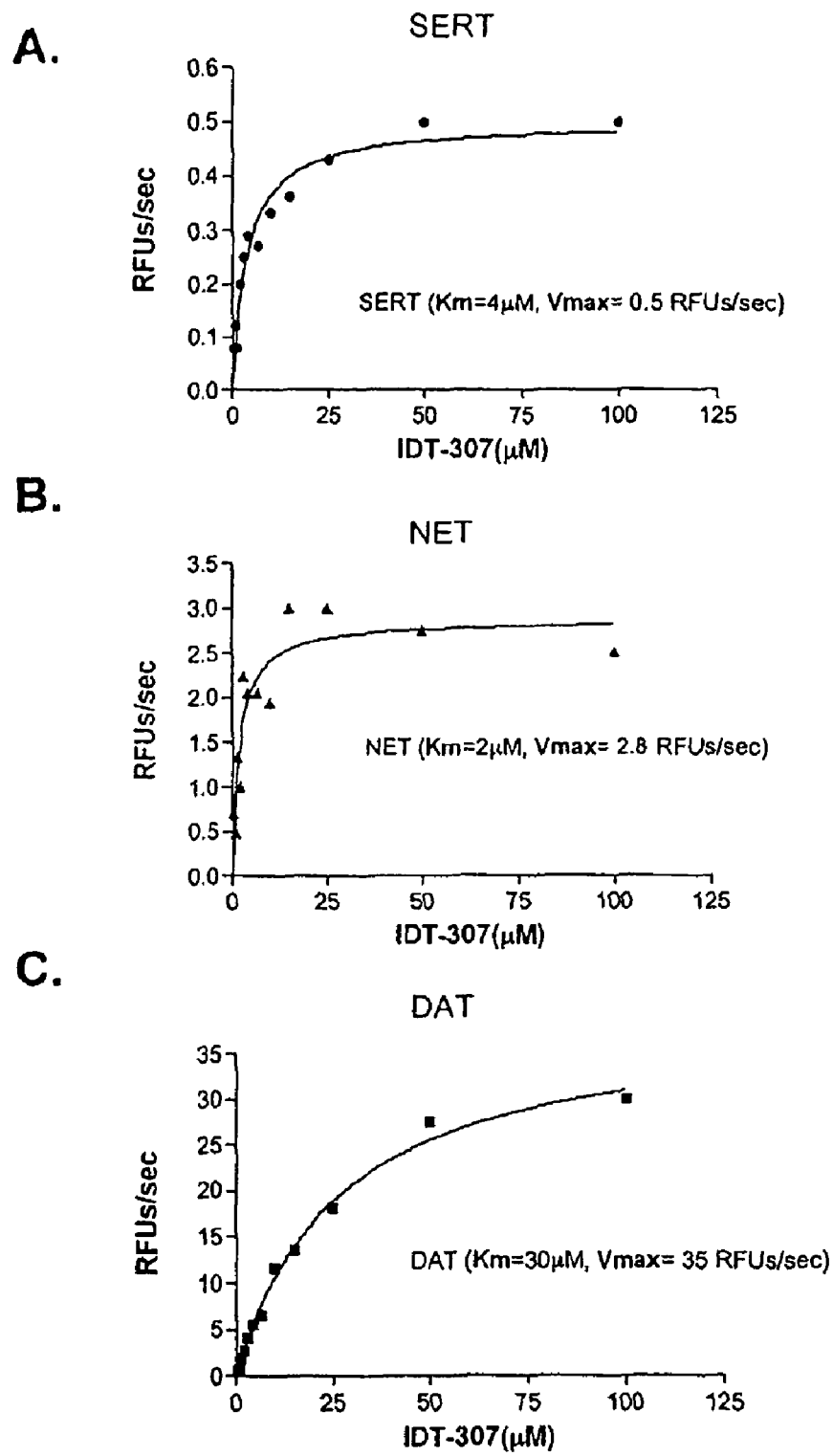
FIGS. 5A-C—Kinetics of IDT307 accumulation in hSERT using the FlexStation™ fluorimeter. Kinetics of IDT307 accumulation in hSERT using the FlexStation fluorimeter. hSERT expressing cells were cultured in wells of a 96-well plate until confluent. Increasing concentrations of IDT307 was then added and allowed to accumulate for 10 min. SERT specific accumulation for each concentration of IDT307 was then calculated from specific uptake values (total uptake—inhibitor treated uptake).
Figure 6:
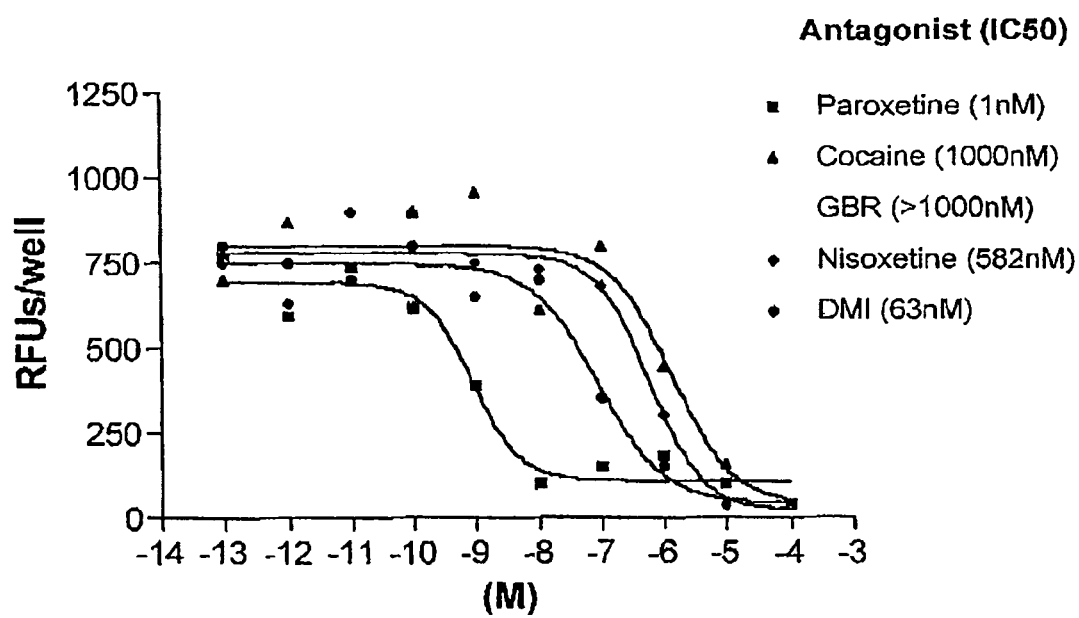
FIG. 6—Antagonist competition for SERT uptake of IDT307. Antagonist competition for SERT uptake of IDT307. LLC cells expressing the hSERT were cultured in a 96-well plate until confluent. Increasing concentrations of paroxetine, cocaine, GBR, nisoxetine, and DMI ($10^{-13}$ to $10^{-4}$) were then added to the wells for 10 min. Next, IDT307 (10 μM) was added to each well. After a 5 min incubation fluorescence values for IDT307 uptake were measured (using the FLEXstation) at each concentration of each inhibitor from specific uptake values (total uptake—inhibitor treated uptake) using non-linear regression analysis.
Figure 7:
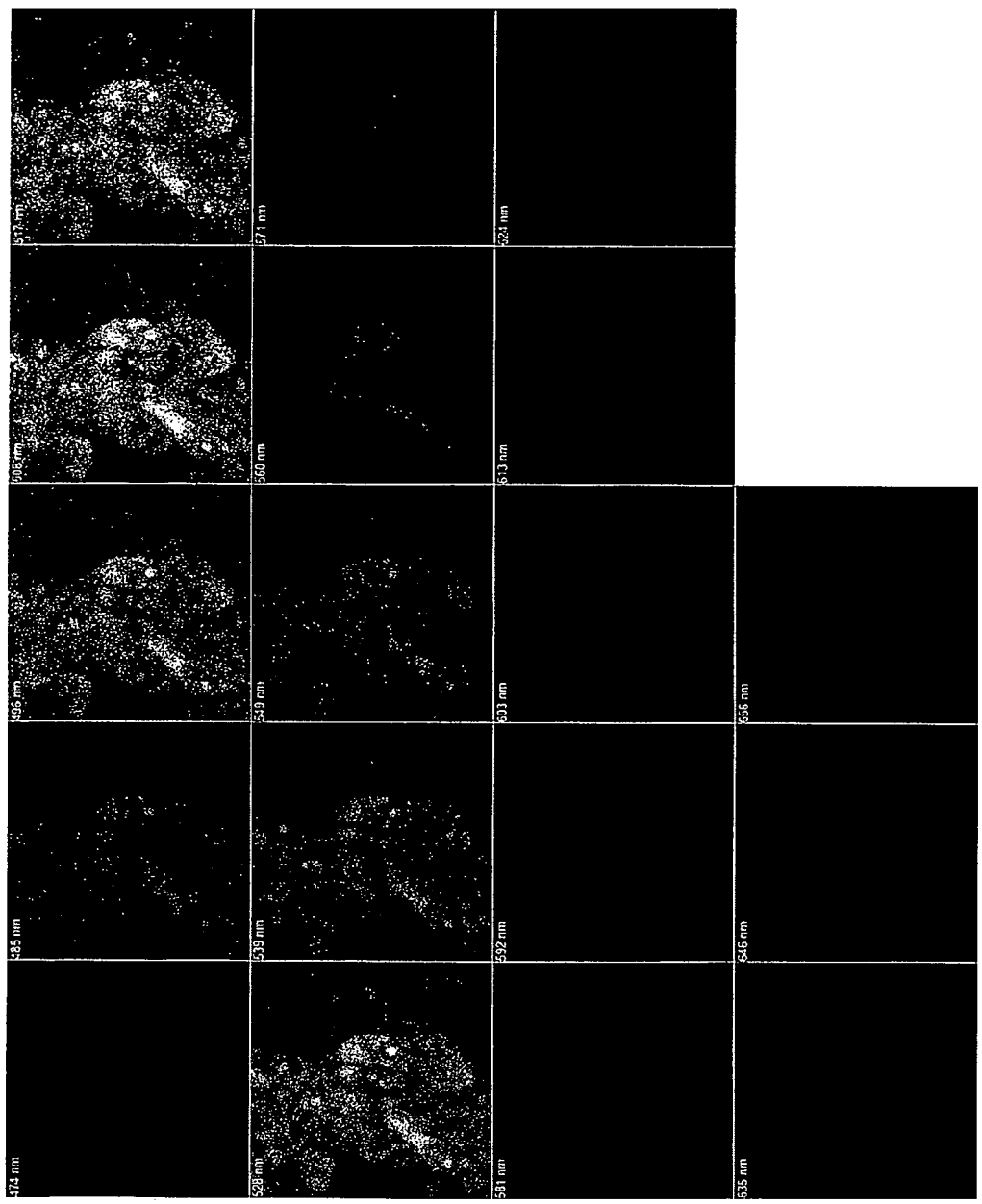
FIG. 7—Imaging IDT307 with Zeiss LSM-510 Confocal Meta Detector. LLC Cells expressing rDAT were exposed to 10 μM IDT307 for 1 hr before rinsing with KRH buffer and imaging with a Zeiss LSM-510 confocal microscope using the meta detector. Quantification of fluorescence at each wavelength for selected regions of interest was performed using Image J analysis software.
Figure 8:
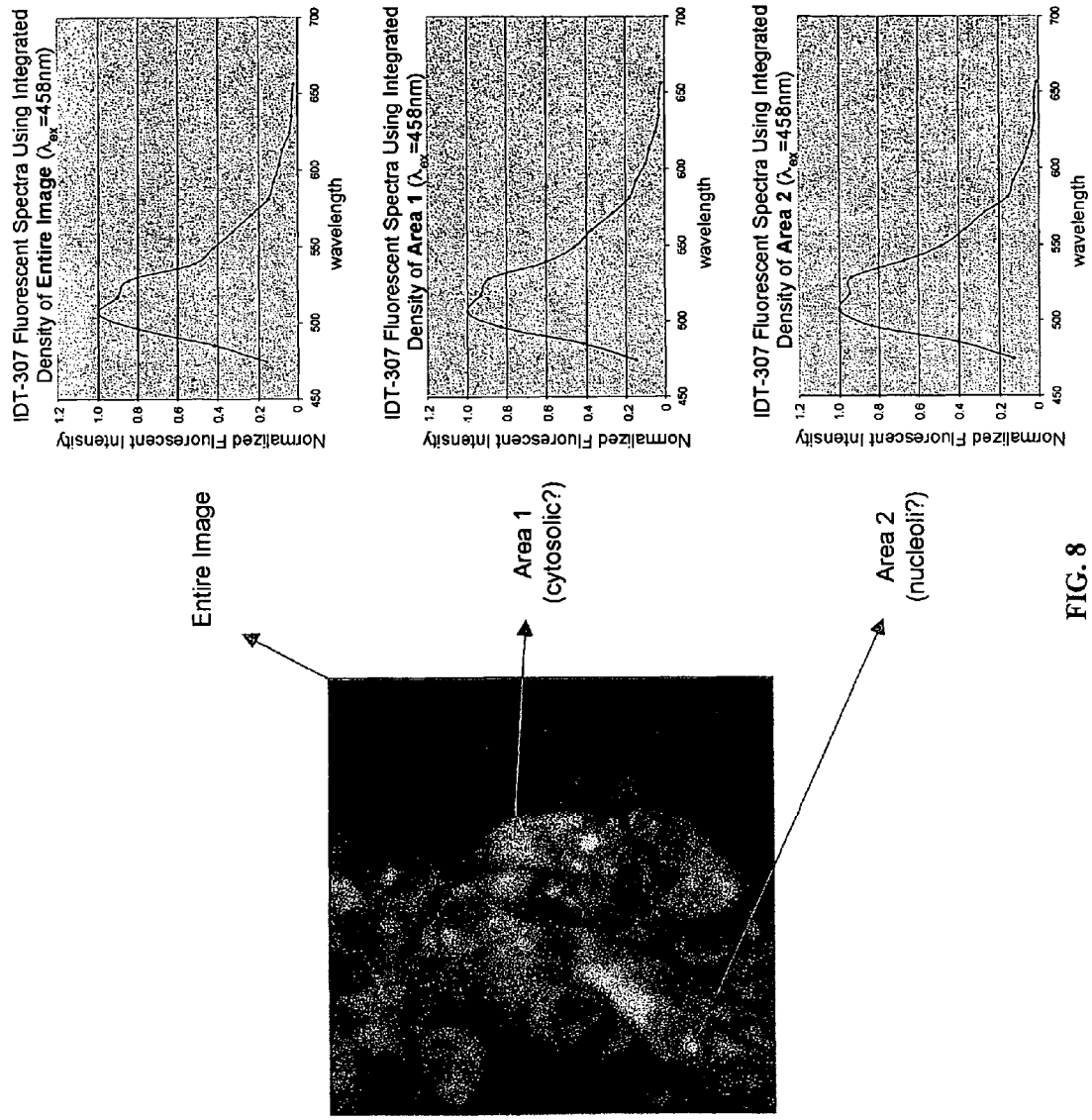
FIG. 8—Fluorescence Spectra of Intracellular IDT307. IDT307 maximum absorption=420 nm, maximum emission=510 nm.

Although neurotransmitter transporters are central to neuronal signal processing and have been implicated in various nervous system related disorders, the art lacks methods that effectively characterize neurotransmitter function and activity. The present inventors have found that the fluorescent substrate IDT307 is transported by NET, DAT and SERT. They have also employed IDT307 in methods to measure neurotransmitter transport mechanisms using fluorescence microscopy. The present inventors have shown that the IDT307 fluorescence assays provide mechanistic information about transport including the kinetics of the Na$^+$- and Cl$^-$-dependent transport and the kinetics involved in blockade of transport by antagonists. In various embodiments, IDT307 may only develop appreciable fluorescence intracellularly, e.g., after transport into the interior of a cell; thus, IDT307 may be used in certain embodiments to measure transporter activity without using a quencher.

A. IDT307 and Analogs Thereof 4-(4-(dimethylamino)phenyl)-1-methylpyridinium iodide, referred to herein as IDT307, is a dye with optical activity that has been discussed by a number of different researchers (Bulgarevich et al., 1992; Kuo, 1978; Coe et al., 2003; Zauhar et al., 1995; Lyapustina et al., 1993). Using time-resolved fluorescence microscopy, the present inventors have demonstrated IDT307 accumulation in human embryonic kidney cells (HEK) expressing human norepinephrine (NE) transporters (hNET). IDT307 accumulation has sub-mM potency for HNET, DAT and SERT, and is sensitive to inhibitors of these transporters. IDT307 fluorescent microscopy permits localization of transport activity in single cells and neuronal processes. The IDT307 fluorescent microscopy methods of the invention also permits analysis of many cells, while retaining information about single cells. The IDT307 fluorescence assays of the invention provide detailed mechanistic information about transport. For example, temporal and spatial resolution of transport, transport kinetics, affinity for substrate, turnover rates, surface expression, and binding constants may be measured. Furthermore, features such as voltage dependence of neurotransmitter accumulation can be assessed under voltage clamp using IDT307 fluorescent microscopy.

Also encompassed are analogs of IDT307, as described below:

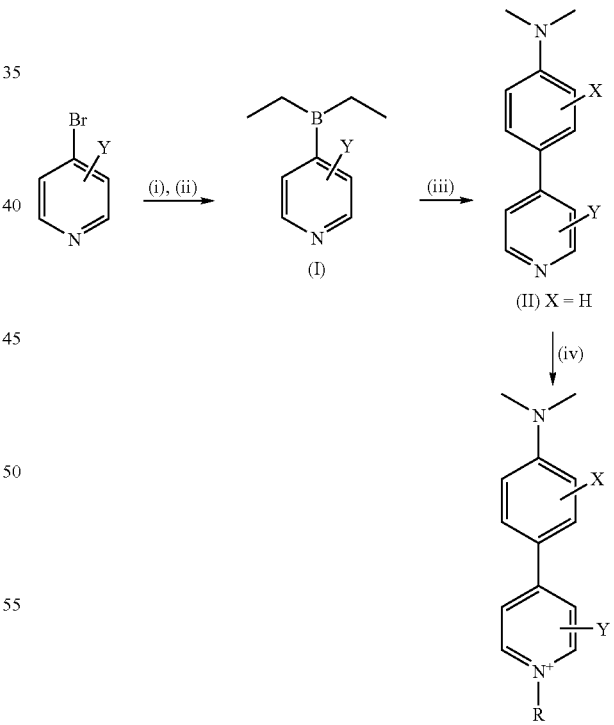

(III) IDT307 R = Me, X = H, Y = H
(IV) IDT321 R = Et, X = H, Y = H
(V) IDT322 R = nPr, X = H, Y = H
(X) IDT326 R = Me, X = Me, Y = H
(XII) IDT330 R = Me, X = F, Y = H

Legend for Scheme 1: (i) nBuLi; (ii) MeOBEt$_2$; (iii) PPh$_3$Pd, Bu$_4$NBr, KOH, 4-Bromo-N,N-dimethylaniline derivative; (iv) alkyl or aryl halide.

In the structure found in the lower right-hand corner of Scheme 1, the substituent X may be one of the following: alkyl, specifically $CH_3$, $CH_2CH_3$, propyl, isopropyl, n-butyl, secondary butyl, tertiary butyl, pentyl, hexyl and other alkyl functionalities (e.g., a $C_{1-12}$ alkyl); fluorinated alkyl derivatives, specifically $CF_3$, $OCF_3$, $SCF_3$, $SO_2CF_3$; nitro, CN, SCN, OCN, amino, N-alkyl amino, N,N-dialkyl amino, F, Br, I, Cl, furyl, thiophenyl, pyridyl, piperidyl, phenyl, napthyl, OH, OR (where R=alkyl), SH, SR (where R=alkyl), $CONH_2$, CONHR (where R=alkyl), $SO_2NH_2$, $SO_2NHR$ (where R=alkyl), COR (where R=alkyl). In embodiments where R is an alkyl, R may be, e.g., a $C_{1-12}$ or a $C_{1-6}$ alkyl.

The phenyl ring may be mono-substituted, di-substituted, tri-substituted, or tetra-substituted with any combination of these substituents. The dimethyl-amino functionality may be ortho, meta or para with respect to the pyridyl ring and the pyriyl nitrogen may be ortho, meta or para with respect to the phenyl ring.

The substituent Y may be one of the following: alkyl, specifically $CH_3$, $CH_2CH_3$, propyl, isopropyl, n-butyl, secondary butyl, tertiary butyl, pentyl, hexyl and other alkyl functionalities; fluorinated alkyl derivatives, specifically $CF_3$, $OCF_3$, $SCF_3$, $SO_2CF_3$; nitro, CN, SCN, OCN, amino, N-alkyl amino, N,N-dialkyl amino, F, Br, I, Cl, furyl, thiophenyl, pyridyl, piperidyl, phenyl, napthyl, OH, OR (where R=alkyl), SH, SR (where R=alkyl), $CONH_2$, CONHR (where R=alkyl), $SO_2NH_2$, $SO_2NHR$ (where R=alkyl), COR (where R=alkyl). In embodiments where R is an alkyl, R may be, e.g., a $C_{1-12}$ or a $C_{1-6}$ alkyl.

The pyridyl ring may be mono-substituted, di-substituted, tri-substituted, or tetra-substituted with any combination of these substituents. The substituent R may be alkyl, aryl, or benzyl.

B. Neurotransmitter Transporters

As described earlier, neurotransmitter transporters are responsible for the uptake of neurotransmitters from the synaptic cleft and thereby are responsible for the regulation of neurotransmission. Transporter proteins in the plasma membranes of neurons and glia also participate in vital nutrient and osmolyte acquisition. Neurotransmitter transporters are typically ion dependent, have high-affinity/specificity for one neurotransmitter, and are temperature and pH sensitive.

Chemical signaling by small molecule neurotransmitters, including DA, NE, E, SE (or 5HT), glutamate, glycine, and GABA, is terminated by transporter-mediated clearance (Rudnick and Clark, 1993). Disruption of transporter function, mediated by genetic mutations, pathological conditions or drugs of abuse, can elevate or rapidly decrease extracellular neurotransmitter levels, perturb presynaptic transmitter homeostasis, and trigger significant alterations in physiology and behavior (Giros et al., 1996; Pelham, 1997). For example, psychoactive agents such as cocaine and the amphetamines compete with the neurotransmitter substrates of the DA, NE, and SE transporters, and their addictive potential has been attributed to DAT blockade (Kuhar et al., 1991). In contrast, NET and SERT antagonists such as imipramine, desipramine, fluoxetine, and sertraline are important agents in the treatment of mood disorders, particularly depression (Barker and Blakely, 1996). Cloning and molecular analysis of neurotransmitter transporters has also shown that genetic mutations and variations are associated with some neuronal disorders and some forms of addictions to substances of abuse.

However, the study of neurotransmitter transporters is severely limited by methods that utilize radiolabeled neurotransmitters or fluorescent analogs of neurotransmitters, all of which have so far been incapable of distinguishing substrate binding from transport. The methods of the present invention provide better understanding of transport with a superior time and spatial resolution and at the level of a single cell, if required. Thus, the present methods provide better characterization of transport mechanics of transporters. This is also relevant in the case of diseases associated with mutations of neurotransmitter transporters as the methods will aid in better understanding the physiological basis of neuronal disorders caused by mutant transport molecules in comparison to normal molecules. The methods of the invention are also important with regard to providing a better understanding of transport changes caused by numerous addictive agents and therapeutic agents that target neurotransmitter transporters.

In addition, the screening methods of the invention, provide rapid screening and identification of novel modulators of neurotransmitter transport. Such assays are also beneficial for screening for modulators of mutant transporters that are expressed in patients with genetic neuronal disorders. It is contemplated that such methods will be useful in identifying therapeutic agents specifically tailored to treat an individual patient. As neurotransmitter transporters are also associated with addiction to drugs of abuse and alcohol the screening methods of the invention are contemplated to provide therapeutic agents that will be effective in reversing such addictions.

i. Norepinephrine Transporters (NET)

NET is a member of a large family of $Na^+$ and $Cl^-$ dependent transporters (Blakely et al., 1991; Masson et al., 1999), exhibits a sub-millimolar substrate potency and can concentrate NE against its concentration gradient. NET accumulates NE by coupling the substrate and co-transported ions at a proposed stoichiometry of $1NE/1Na^{2+}/1Cl^-$ (Ressler and Nemeroff, 1999; Ramamoorthy et al., 1993; Bonisch and Harder, 1986).

Approximately 70-90% of the NE released into synapses is estimated to be cleared using NET. NE uptake by NET is competitively inhibited by various drugs of abuse such as amphetamine and cocaine, and antidepressants (e.g., desipramine, imipramine, venlafaxine, mirtazapine, reboxetine, bupropion), thereby resulting in an elevation of the synaptic concentrations of NE which results in potentiation of the activation of postsynaptic receptors. Other evidence has shown that treatments with drugs that alter noradrenergic transmission can cause an up- or down-regulation of NET, which in turn causes changes in the sensitivity to endogenous catecholamines.

NET was isolated by expression cloning in 1991, and the gene was found to be located on human chromosome 16q 12.2 (Pacholczyk et al., 1991). The NET gene is encoded by 14 exons, which span 45 kb from the start to the stop codon (Porzgen et al., 1996). The nucleotide and deduced amino acid sequence of the transporter predict a protein of 617 amino acids, containing 12 membrane-spanning domains. The organization of the protein is highly homologous to that of other neurotransmitter transporters including those transporting dopamine, epinephrine, serotonin and gamma-aminobutyric acid (GABA), which are members of a family of sodium- and chloride-dependent transport proteins in the plasma membranes of neurons and glial cells. Analysis of the NET gene and protein has facilitated the investigation of its potential role in psychiatric and other neuronal disorders. At least 13 genetic variants of NET have been identified so far by methods such as single-stranded conformational polymorphism analysis (Stober et al., 1996; Samochowiec et al., 2001; Kitayama et al., 2001).

ii. Dopamine Transporter (DAT)

The dopamine transporter (DAT) is a member of the subfamily of monoamine transporters with numerous common topological structures and significant amino acid sequence homology. DAT has been identified as located on the distal end of chromosome 5 (5 p15.3) (Giros et al., 1992). Kawarai et al., (1997), isolated and characterized the human DAT gene (hDAT) including about 1 kb of 5'-flanking region. The hDAT gene spans over 64 kb, consisting of 15 exons separated by 14 introns. The intron-exon structure of the hDAT gene is most similar to that of the human NET gene. Promoter sequence analysis demonstrated a 'TATA'-less, 'CAT'-less and G+C-rich structure. Two E box and several Sp-1-binding sites exist in the promoter region. These structural features are similar to that of the human D1A dopamine receptor gene and the human monoamine oxidase A gene. The DAT gene encodes for a 620-amino acid protein with a calculated molecular weight of 68,517 (Giros et al., 1992) and is associated with numerous neuropsychiatric disorders (Bannon, 2001). Examples of neurological diseases involving dopamine transporter function include schizophrenia, addiction disorders, attention deficit hyperactivity disorder (ADHD), psychoses, Tourette's syndrome, and Parkinson's disease.

iii. Serotonin Transporter (SERT)

The serotoninergic system modulates numerous behavioral and physiological functions and has been associated with control of mood, emotion, sleep and appetite. Synaptic serotonin (SE), also called 5-hydroxytryptamine or 5HT, concentration is controlled by the serotonin transporter (SERT) which is involved in reuptake of serotonin into the pre-synaptic terminal. The cloning of the human SERT protein by Ramamoorthy et al., (1993), shows that human SERT is encoded by a single gene that is localized to chromosome 17q11.1-17q12 and encodes for a 630-amino acid protein. The hSERT is a $Na^+$- and $Cl^-$-coupled serotonin transporter and has been found to be expressed on human neuronal, platelet, placental, and pulmonary membranes (Ramamoorthy et al., 1993).

The SERT has been associated with depression and anxiety (Soubrie, 1988; Barnes, 1988); obesity (Blundell, 1986; Silverstone et al., 1986); alcoholism (Gill et al., 1987; Naranjo et al., 1987); post-anoxic intention myoclonus (Van Woert, et al., Monogr, 1976); acute and chronic pain (Le Bars, 1988); as well as sleep disorders (Koella, 1988). SERT has also been shown to mediate behavioral and/or toxic effects of cocaine and amphetamines (Ramamoorthy et al., 1993). A variety of specific serotonin reuptake inhibitors (SSRIs) such as fluoxetine and paroxetine have been developed for the treatment of depression (reviewed in Schloss, 1998). However, as Schloss points out, the art lacks a detailed understanding of the mode of action of these antidepressant drugs on their target, the SERT protein. Furthermore, although several drugs that target the SERT have been identified the art still lacks effective drugs for the treatment and alleviation of depression and other neurological disorders.

Recent research has shown that polymorphisms in the promoters of SERT's are a risk factor for susceptibility to depression (Neumeister et al., 2002). Other studies have also shown the association of variants of SERT's to other disorders. For example, association for allele 12 of the variable number tandem repeat (VNTR) in the second intron of the SERT gene and schizophrenic disorders has been shown (Tsai et al., 2002).

C. Methods of Measurement of Transport

The present invention provides methods for the measurement of transport of neurotransmitter transporters including the transporters for biogenic amines such as serotonin, dopamine, epinephrine, norepinephrine. It is contemplated that these methods are also applicable to transporters of the amino acids neurotransmitters such as L-glycine and L-glutamate, L-aspartate, and g-aminobutyric acid (GABA). In some embodiments, the present invention provides a novel and rapid method for analysis of transport by a neurotransmitter transporter that comprises the measurement of uptake and/or accumulation of IDT307 that is specifically taken up by the transporter. The methods of measurement involve fluorescence microscopy. In other embodiments, other fluorescent substrates may be used, some of which are contemplated to be analogs of IDT307 and others are contemplated to be analogs of other native neurotransmitters.

i. Microscopy

Fluorescent microscopy is used to measure transport using IDT307 which is a fluorescent substrate for several neurotransmitter transporters. Cells that either endogenously or exogenously express a neurotransmitter are isolated and plated on glass bottom Petri-dishes or multi-well plates that may typically be coated with poly-L-lysine or any other cell adhesive agent. Cells are typically cultured for three or more days. The culture medium is then aspirated and replaced with buffer and the cells are mounted on a Zeiss 410 confocal microscope. During the confocal measurement cells remain without IDT307 for approximately thirty seconds. Background autofluorescence is established by collecting images for ten seconds prior to the addition of IDT307.

ii. Fluorescence Anisotropy Measurements

To evaluate IDT307 binding to the surface membranes, cells expressing a neurotransmitter transporter may be exposed to IDT307 with horizontal polarizer, with the polarizer rapidly switching to the vertical position. Cells may be imaged with alternating polarizations for 3 minutes to measure light intensity in the horizontal $(I_h)$ and vertical $(I_v)$ positions in order to calculate the anisotropy ratio, $r=(I_v-gI_h)/(I_v+2 g I_h)$. The factor g may be determined by using a half wave plate as described by Blackman et al. (1996). In this formulation, $r=0.4$ implies an immobile light source. Surface anisotropy can be measured at the cell circumference over 1 pixel width (0.625 mm). Cytosolic anisotropy can be measured near the center of the cell, approximately 5 pixel widths from the membrane.

iii. Image Analysis

The fluorescent images may be processed using suitable software. For example, fluorescent images were processed using MetaMorph imaging software (Universal Imaging Corporation, Downington Pa.). Fluorescent accumulation was established by measuring the average pixel intensity of time resolved fluorescent images within a specified region identified by the DIC image. Average pixel intensity is used to normalize among cells.

iv. Single Cell Fluorescence Microscopy

In some embodiments, the invention provides measurement of transporter characteristics at the single-cell level. Single-cell fluorescence microscopy provides a powerful assay to study rapid neurotransmitter uptake kinetics from single cells.

v. Automation

The inventors further contemplate that all methods disclosed herein are adaptable to high-throughput formats using robotic fluid dispensers, multi-well formats and fluorescent plate readers for the identification of neurotransmitter transport modulators.

vi. Other Methods

In addition, uptake and accumulation of the neurotransmitter may be also characterized by other methods known in the art such as (a) in vivo inhibition by known agonists and antagonists of the neurotransmitter transporter; (b) knockout models, where a particular gene that modulates in or otherwise suspected to be involved in transport is omitted (for example, DAT knockouts as described in Giros et al., 1996) (c) slice electrophysiology, in which particular neurons are identified and subjected to analysis in situ.

D. Screening for Neurotransmitter Modulators

Defects in neurotransmitter transporters are associated with various nervous system disorders including depression, stress disorders, attention deficit disorder, Parkinson's disease, anxiety, obesity, several sleep related disorders and certain neurodegenerative diseases (Edwards, 1993). For example, biogenic amine transporters which are responsible for inactivation of dopamine, norepinephrine, serotonin and epinephrine are major targets for multiple psychoactive substances including cocaine, amphetamines, methylphenidate (Ritalin™), tricyclic antidepressants and the SSRIs such as fluoxetine (Prozac™). However, there is still a need in the art to identify other modulators of neurotransmitter transporters given the large number of neurological and psychiatric diseases that are associated with transporter defects.

The present invention provides methods for identifying modulators of the function of neurotransmitter transporters. These methods may comprise random screening of large libraries of candidate substances. Alternatively, the methods may be used to focus on particular classes of compounds selected with an eye towards structural attributes that are believed to make them more likely to modulate the function of a particular neurotransmitter transporter.

By function, it is meant that one may assay for uptake, accumulation, or clearance of the neurotransmitter, its analog or derivative or for some biological aspect of neurotransmitter release, uptake or clearance—in this case, IDT307 in particular. Micro-dialysis and amperometry may be used to assay transporter function in vivo (Giros et al., 1996; Galli et al. 1998).

To identify a neurotransmitter transporter modulator, one generally will determine the function of the neurotransmitter transporter in the presence and absence of the candidate agent, a modulator defined as any agent that alters function. For example, a method generally comprises:
  a) providing a candidate modulator;
  b) contacting the candidate modulator with a cell expressing a neurotransmitter transporter, or a cell extract or cell membrane preparation that comprises the neurotransmitter transporter, or a suitable experimental animal;
  c) measuring one or more characteristics of the transporter, cell, cell extract or cell membrane preparation, or animal, that reflects the function or activity of the transporter; and
  d) comparing the characteristic measured in step (c) with the characteristic of the compound, cell, cell extract or cell membrane preparation, or animal in the absence of the candidate modulator,
wherein a difference between the measured characteristics indicates that the candidate modulator is, indeed, a modulator of the neurotransmitter transporter.

Comparing the characteristic measured as described in the steps above includes measurement of uptake, accumulation, binding, ion dependence, antagonist block, dependence on expression level, voltage- and $Ca^{2+}$-dependence, and/or clearance of IDT307.

Assays may be conducted in cell free systems such as cellular extracts, cell membrane preparations which may be prepared by lysing cells, in isolated cells, in cells that express endogenous a neurotransmitter transporter, in cells that are genetically engineered to express a neurotransmitter transporter, in cells that exogenously or endogenously express mutant or functionally deficient transporters, or in organisms including transgenic animals or animal models of diseases wherein the disease is associated with neurotransmitter transporters. Thus, knockouts for neurotransmitter transporters may be used (Giros et al., 1996; Sora et al., 2001). It will, of course, be understood that all the screening methods of the present invention are useful in themselves notwithstanding the fact that effective candidates may not be found. The invention provides methods for screening for such candidates, not solely methods of finding them.

i. Modulators

As used herein the term "candidate substance" or "candidate agent" refers to any molecule that may potentially inhibit or enhance the activity of a neurotransmitter transporter. The candidate substance may be a protein or fragment thereof, a small molecule, or even a nucleic acid molecule. It may prove to be the case that the most useful pharmacological compounds will be compounds that are structurally related to the known neurotransmitter transporter modulators, agonists and antagonists such as cocaine, amphetamines, monoamine oxidase inhibitors, imipramine and the like. Using lead compounds to help develop improved compounds is known as "rational drug design" and includes not only comparisons with known inhibitors and activators, but also predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate agents may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on the neurotransmitter transporter. Regardless of the type of inhibitor or activator identified by the present screening methods, the effect of the inhibition or activation by such a compound results in a difference as compared to that observed in the absence of the added candidate substance.

ii. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay in this invention is the use of cellular extracts that comprise a neurotransmitter, these may be cell membrane preparations that comprise a neurotransmitter transporter.

Another example is a cell-binding assay. While not directly addressing function, the ability of a modulator to bind to a target molecule (in this case the neurotransmitter transporter) in a specific fashion is strong evidence of a related biological effect. For example, binding of a molecule to a neurotransmitter transporter may, in and of itself, be inhibitory, due to steric, allosteric or charge-charge interactions. The neurotransmitter transporter protein may be either free in solution, fixed to a support, expressed in or on the surface of a cell. Either the neurotransmitter transporter or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

iii. In Cyto Assays

The present invention also contemplates the screening of agents for their ability to modulate neurotransmitter transporter in cells. Various cells and cell lines can be utilized for such screening assays as long as the cell expresses a neurotransmitter transporter. This includes cells specifically engineered to expresses a neurotransmitter transporter. Such cells and nucleic acid vectors are described in several sections infra as well as U.S. Pat. Nos. 5,312,734, 5,418,162, and 5,424,185, the contents of which are all incorporated herein by reference.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

iv. In Vivo Assays

In vivo assays involve the use of various animal models, including transgenic animals that have been engineered to have specific defects, or carry markers that can be used to measure the ability of a candidate agent to reach and effect expression of neurotransmitter transporters in different cells within the organism. Due to their size, ease of handling, and information on their physiology and genetic make-up, mice and/or *C. elegans* are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate agents are administered to an animal, and the ability of the candidate agent(s) to alter one or more characteristics that are a result of neurotransmitter function or activity, as compared to a similar animal not treated with the candidate agent(s), identifies a modulator. The characteristics may be any of those discussed above with regard to the function of a particular neurotransmitter such as change in neurotransmission, change in the activity of some other downstream protein due to a change in neurotransmission, or instead a broader indication such as behavior of an animal etc.

The present invention provides methods of screening for candidate agents that modulate neurotransmitter transporter function or activity. In these embodiments, the present invention is directed to a method for determining the ability of a candidate agent to modulate neurotransmitter transporter function, generally including the steps of: administering a candidate substance to the animal; and determining the ability of the candidate substance to change one or more characteristics of the neurotransmitter transporter.

Methods for in vivo imaging are described in Herrera & Banner (1990), and in Herrera et al. (1990), (both incorporated herein by reference). In situ methods for analysis are described in Pietruck & Ullrich (1995) and Rohlicek & Ullrich (1994), (also incorporated herein by reference). These methods may be suitably modified with the other teachings of this specification to perform the in vivo assays using IDT307.

Treatment of these animals with test agents will involve the administration of the agent, in an appropriate form, to the animal. Administration will be by any route that could be utilized for clinical or non-clinical purposes, including but not limited to oral, nasal, buccal, or even topical. Alternatively, administration may be by parenteral methods such as intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

F. Vectors for Delivery and Expression of Neurotransmitter Transporters

Within certain embodiments, expression vectors are employed to express a neurotransmitter transporter in a cell, for example, an DAT, NET, or SERT. The specification provides a description of transformation of HEK cells to express exogenous NET as one example infra. Furthermore, U.S. Pat. Nos. 5,312,734, 5,418,162, and 5,424,185, both incorporated herein by reference, describe nucleic acids, vectors, and host cells used to express various neurotransmitter transporters in cells. As will be understood by one of skill in the art, the invention is not limited to any particular type of neurotransmitter transporter or cell type and expression vectors encoding any neurotransmitter transporter can be used in any cell type. Additionally, as set forth above one may also use mutant versions, isoforms, and other variants of any neurotransmitter transporter in the methods of the invention.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide. Gene transfer may rely on viral elements as in the case of viral vectors, or non-viral means including lipids (liposomes, nanoparticles), electroporation, etc.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

IDT307. The synthetic scheme used to synthesize IDT 307 is outlined in Scheme 1, above. Briefly 4-bromo-pyridine was converted to diethyl (4-pyridyl)borane (I) via a reaction of 4-lithiopyridine with diethylmethoxyborane. Resulting in a 20% yield of (I). This was coupled to 4-dimethyl amino bromo benzene using the method developed by Ishikura (Ishikura et al., 1985). Tetrakis(triphenylphosphine) palladium (0) catalyst was added to (4-pyridyl)borane, tetrabutylammonium bromide, powdered KOH and 4-dimethyl amino bromo benzene. This mixture was dissolved in THF and heated at reflux under a nitrogen atmosphere. Resulting in N,N-dimethyl-4-(pyridine-4-yl) aniline (II) in a 17% yield. The pyridine ring was methylated by refluxing (II) in acetonitrile in the presence of methyl iodide and IDT 307 (III) crystallized upon cooling resulting in a 65% yield of the desired compound.

Diethyl (4-pyridyl borane) (I). N-Butyllithium (1.6M in hexanes, 20 ml) was added to dry ether (100 ml) and cooled to −40° C. under nitrogen. The solution was stirred and a solution of 4-Bromopyridine (32 mmols) dissolved in dry ether was added drop wise. The ethereal solution was stirred for 30 minutes at −40° C. then cooled to −70° C. Diethyl methoxy borane (4.6 ml) dissolved in dry ether (50 ml) was added drop wise and the mixture was allowed to warm to room temperature over night. Ethyl acetate (100 ml) and brine (70 ml) were added to the resulting brown solution and the organic layer was separated. This was dried over magnesium sulfate, filtered and evaporated to yield a brown tar. The product was purified by column chromatography on silica eluted with toluene to yield (0.94 g, 6.4 mmols) of Diethyl (4-pyridyl borane) (I) as a white solid.

N,N-dimethyl-4-(pyridine-4-yl) aniline (II). Diethyl (4-pyridyl borane) (1.3 g, 9 mmols) and 4-bromo-N,N-dimethylaniline (2.65 g, 13 mmols) were mixed in tetrahydrofuran (50 ml). To this potassium hydroxide (2.81 g, 50 mmols), tetrabutylammonium bromide (1.42 g, 4 mmols) and tetrakis (triphenylphosphine)palladium(0) (0.51 g, 0.4 mmols) was added. This mixture was heated at reflux for 18 hours under nitrogen then cooled to ambient temperature. Ethyl acetate (100 ml) and brine (50 ml) were added and the organic solution was separated. This was dried over magnesium sulfate filtered and evaporated to yield a yellow solid. The product was purified by column chromatography on silica eluted with ethyl acetate. This gave N,N-dimethyl-4-(pyridine-4-yl) aniline (II) (0.3 g, 1.5 mmols) as a white solid.

4-(4-(dimethylamino)phenyl)-1-methylpyridinium iodide (IDT307) (III). N,N-dimethyl-4-(pyridine-4-yl) aniline (0.15 g, 7.6 mmols) was dissolved in acetonitrile (50 ml) and methyl iodide (4 ml) was added. The mixture was heated at reflux for 4 hrs then cooled to ambient temperature. IDT307 (0.17 g, 5 mmols) crystallized upon standing and was removed via filtration. $^1$H NMR (DMSO-d6) δ 3.40 (s, 6H), 4.25 (s, 3H), 6.92 (d, 2H), 8.06 (d, 2H), 8.38 (d, 2H), 8.80 (d, 2H).

Example 2

IDT321. Was prepared by refluxing N,N-dimethyl-4-(pyridine-4-yl) aniline (II) in acetonitrile in the presence of ethyl iodide. Upon cooling diethyl ether was added and the product crystallized resulting in a 18% yield of 4-(4-(dimethylamino) phenyl)-1-ethylpyridinium iodide (IDT321) (IV).

4-(4-(dimethylamino)phenyl)-1-ethylpyridinium iodide (IDT321) (IV). N,N-dimethyl-4-(pyridine-4-yl) aniline (0.1 g, 5.5 mmols) was dissolved in acetonitrile (50 ml) and ethyl iodide (4 ml) was added. The mixture was heated at reflux for 4 hours then cooled to ambient temperature. Diethylether (50 ml) was added IDT321 (0.035 g, 0.9 mmols) crystallized upon standing and was removed via filtration. $^1$H NMR (DMSO-d6) δ 1.50 (t, 3H), 3.40 (s, 6H), 4.50 (q, 2H), 6.95 (d, 2H), 8.05 (d, 2H), 8.35 (d, 2H), 8.90 (d, 2H).

Example 3

IDT322. Was prepared by refluxing N,N-dimethyl-4-(pyridine-4-yl) aniline (II) in acetonitrile in the presence of ethyl iodide. After which the solution was cooled to room temperature. Ether was added and the product crystallized resulting in a 29% of 4-(4-(dimethylamino)phenyl)-1-propylpyridinium iodide (IDT322) (V).

4-(4-(dimethylamino)phenyl)-1-propylpyridinium iodide (IDT322) (V). N,N-dimethyl-4-(pyridine-4-yl)aniline (0.2 g, 11 mmols) was dissolved in acetonitrile (50 ml) and propyl iodide (4 ml) was added. The mixture was heated at reflux for 4 hours then cooled to ambient temperature. Diethylether (50 ml) was added IDT322 (0.11 g, 2.9 mmols) crystallized upon standing and was removed via filtration. $^1$H NMR (DMSO-d6) δ 1.40 (t, 3H), 1.92 (q, 2H) 3.40 (s, 6H), 4.45 (t, 2H), 6.85 (t, 2H), 8.02 (d, 2H), 8.39 (d, 2H), 8.82 (d, 2H).

Example 4

IDT326. Initially 4-Bromo-3-methylaniline was methylated using dimethyl sulfate resulting in a 29% yield of 4-dimethyl amino-2-methyl bromo benzene (VI). This was then coupled to diethyl (4-pyridyl) borane (I) using a tetrakis triphenyl phosphine palladium (0) catalyst to give N,N,3-trimethyl-4-(pyridin-4-yl)aniline (VII) in a 18% yield. This was methylated by refluxing (VII) in acetonitrile for 2 hours and crystalised out of a 50:50 mixture of acetonitrile: diethyl ether to give 4-(4-(dimethylamino)-2-methylphenyl)-1-methylpyridinium iodide (X) IDT326 in a 21% yield.

4-dimethyl amino-2-methyl bromo benzene (VI). 4-Bromo-3-methyl aniline (32.32 g, 0.174 mols) was added to deionised water (30 ml) in a 500 ml round bottomed flask and cooled with an ice water bath. Dimethyl sulfate (16.5 ml) was added drop wise maintaining the temperature below 10° C. and the resulting mixture was stirred for 30 minutes. Then the mixture was neutralized with potassium hydroxide solution (25%). After which dimethyl sulfate (16.5 ml) was added drop wise and the solution was stirred for 1 hour. The solution was neutralized with potassium hydroxide (25%) and dimethyl sulfate (8.25 ml) was added drop wise. This solution was stirred for a further hour then basified to pH 9 with potassium hydroxide (25%). The solution was extracted with diethyl ether (3×100 ml) and the combined organic solutions were dried over magnesium sulfate. This was filtered and evaporated under reduced pressure. The resulting oil was added to acetic anhydride (50 ml) and stirred at room temperature for 1 hour. Then deionised water (100 ml) was added and the mixture was heated at reflux for 1 hr. The solution was cooled and basified with aqueous potassium carbonate. Then it was extracted into diethyl ether (3×100 ml) and dried over magnesium sulfate. The solution was filtered and evaporated under reduced pressure. The crude product was purified by column chromatography on silica eluted with a 50:50 mixture of ethyl acetate:hexanes to yield 29% of (VI) as a pink solid.

N,N,3-trimethyl-4-(pyridin-4-yl)aniline (VII). Diethyl (4-pyridyl borane) (1.3 g, 9 mmols) and 4-dimethyl amino-2-methyl bromo benzene (2.78 g, 13 mmols) were mixed in tetrahydrofuran (50 ml). To this potassium hydroxide (2.81 g, 50 mmols), tetrabutylammonium bromide (1.42 g, 4 mmols) and tetrakis(triphenylphosphine)palladium(0) (0.51 g, 0.4 mmols) was added. This mixture was heated at reflux for 18 hrs under nitrogen then cooled to ambient temperature. Ethyl acetate (100 ml) and brine (50 l) were added and the organic solution was separated. This was dried over magnesium sulfate filtered and evaporated to yield a yellow solid. The product was purified by column chromatography on silica eluted with ethyl acetate. This gave N,N,3-trimethyl-4-(pyridin-4-yl)aniline (VII) (0.5 g, 2.4 mmols) as a yellow solid.

4-(4-(dimethylamino)-2-methylphenyl)-1-methylpyridinium iodide (X) IDT326. N,N,3-trimethyl-4-(pyridine-4-yl)aniline (0.2 g, 0.9 mmols) was dissolved in acetonitrile (50 ml) and methyl iodide (3 ml) was added. The mixture was heated at reflux with stirring for 2 hrs cooled and evaporated to a volume of 10 ml. Then diethyl ether (50 ml) was added and the product crystallized resulting in (0.068 g, 0.19 mmols) of 4-(4-(dimethylamino)-2-methylphenyl)-1-methylpyridinium iodide as a red solid. $^1$H NMR (DMSO-d6) δ 2.40 (s, 3H), 3.00 (s, 6H), 4.30 (s, 3H), 6.70 (m, 2H), 6.90 (d, 2H), 8.10 (d, 2H), 8.85 (d, 2H).

Example 5

IDT330. 4-Bromo-2-fluoroaniline was methylated by treating it with dimethylsulphate to give a 26% yield of 4-Bromo-2-fluoro-N,N-dimethylaniline (XI) as a red oil. The resultant 4-Bromo-2-fluoro-N,N-dimethylaniline was coupled to diethyl (4-pyridyl) borane (I) using a tetrakis triphenyl phosphine palladium (0) catalyst to give 2-Fluoro-N,N-dimethyl-4-(pyridin-4-yl)aniline (XII) in a 44% yield. This was methylated by refluxing it in acetonitrile in the presence of methyl iodide and the product 4-(4-(dimethylamino)-3-fluorophenyl)-1-methylpyridinium iodide (XIII) IDT330 was obtained in a 21% yield.

4-Bromo-2-fluoro-N,N-dimethylaniline (XI). Deionised water (10 ml) was added to 4-bromo-2-fluoroaniline (10 g, 53 mmols) in a 500 ml round bottomed flask. This was cooled to 5° C. in an ice water bath. Then dimethyl sulfate (5 ml) was added drop wise with stirring. The resulting mixture was stirred for 30 min and neutralized with 25% KOH solution. Another 5 ml of dimethyl sulfate was added and the mixture was stirred for an hour after which it was neutralized with 25% KOH and 2.5 ml of dimethyl sulfate was added drop wise. The mixture was stirred for an hour and basified to pH 8 with 25% KOH. Then it was extracted into diethyl ether (3×100 ml), dried over magnesium sulfate filtered and evaporated. The resulting red oil was added to acetic anhydride (20 ml) and stirred at room temperature for 1 hour. After which deionised water (50 ml) was added and the mixture was heated at reflux for a further hour. The solution was cooled to ambient temperature and neutralized with potassium carbonate. Then it was extracted into diethyl ether (3×100 ml) and this was dried over magnesium sulfate. After which it was filtered and evaporated to yield crude product which was purified using column chromatography on silica eluted with ethyl acetate:hexanes 50:50. This gave the desired product in a 26% yield as a red oil.

2-Fluoro-N,N-dimethyl-4-(pyridine-4-yl)aniline (XII). 4-Bromo-2-fluoro-N,N-dimethyl aniline (2.83 g, 13 mmols), tetrakis triphenyl palladium (0) (0.508 g, 0.4 mmols), diethyl (4-pyridyl borane) (1.3 g, 9 mmols), potassium hydroxide (2.81 g, 50 mmols) and tetrabutylammonium bromide (1.42 g, 4 mmols) were combined in tetrahydrofuran (50 ml). The resulting mixture was heated at reflux for 18 hrs under nitrogen then cooled to ambient temperature. Ethyl acetate (100 ml) and brine (50 ml) were added and the organic solution was separated. This was dried over magnesium sulfate filtered and evaporated to yield a yellow solid. The product was purified by column chromatography on silica eluted with ethyl acetate:hexanes 50:50 to give 0.9 g of 2-Fluoro-N,N-dimethyl-4-(pyridin-4-yl)aniline (XII) in a 44% yield as a pale yellow solid.

4-(4-(dimethylamino)-3-fluorophenyl)-1-methylpyridinium iodide (XIII) IDT330. 2-Fluoro-N,N-dimethyl-4-(pyridin-4-yl)aniline (0.5 g, 2.3 mmols) was dissolved in acetonitrile (50 ml) and methyl iodide (3 ml) was added. The mixture was heated at reflux for 2 hrs. This was cooled to ambient temperature and evaporated the product was purified by recrystallization from ethanol/diethyl ether. To give 0.2 g of 4-(4-(dimethylamino)-3-fluorophenyl)-1-methylpyridinium iodide 21% yield as a red solid. $^1$H NMR (DMSO-d6) δ 3.0 (s, 6H), 4.25 (s, 3H), 7.02 (t, 1H), 7.90 (m, 2H), 8.90 (d, 2H), 8.90 (d, 2H).

All of the compositions and/or methods disclosed and claimed herein can be made and executed without undue experimentation in light of the present disclosure. while the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,312,734
U.S. Pat. No. 5,418,162
U.S. Pat. No. 5,424,185
U.S. Pat. No. 5,670,113
U.S. Pat. No. 6,127,133
U.S. Publn. 20040115703
Aston-Jones et al., *Biol. Psychiatry,* 46:1309-1320, 1999.
Ausubel et al., In: *Current Protocols in Molecular Biology,* John, Wiley and Sons, Inc, New York, 1994.
Axelrod and Kopin, *Prog. Brain Res.,* 31, 21-32, 1969.
Bannon, *Eur. Neuropsychopharmacol.,* 11(6):449-55, 2001.
Barker and Blakely, *Mol. Pharmacol.,* 50(4):957-65, 1996.
Barnes, *Science,* 241:1029-1030, 1988.
Biederman and Spencer, *Biol. Psychiatry,* 46:1234-1242, 1999.
Blackman et al., *Biophys. J.,* 71(1):194-208, 1996.
Blakely et al., *Nature,* 354:66-70, 1991.
Blundell, *Appetite,* 7(1):39-56 1986.
Bonisch and Harder, *Naunyn Schmiedebergs Arch. Pharmacol.,* 334:403-411, 1986.
Bonisch, *Naunyn Schmiedebergs Arch. Pharmacol.,* 327:267-272, 1984.
Bruns, *Methods Enzymol.,* 296:593-607, 1998.
Bulgarevich et al., *Khimiya Geterosiklicheskikh Soedinenii,* 5:625-630, 1992.
Clarkson, et al., *Circulation,* 87:950-962, 1993.
Coe et al., *Advanced Functional Materials,* 13(5):347-357, 2003.
Corey et al., *Proc. Natl. Acad. Sci. USA,* 91:1188-1192, 1994.
Coull et al., *Neuroimage.,* 10:705-715, 1999.
DeFelice and Galli, *Adv. Pharmacol.,* 42:186-190, 1998.
Dow and Kline, *Ann. Clin. Psychiatry,* 9:1-5, 1997.
Edwards, *Ann Neurol.,* 34(5):638-645, 1993.
Fleckenstein et al., *Eur. J. Pharmacol.,* 382:45-49, 1999.
Galli et al., *J. Exp. Biol.,* 198(10):2197-2212, 1995.
Galli et al., *Proc. Natl. Acad. Sci. USA,* 93:8671-8676, 1998.
Gill et al., *Alcoholism II,* 444-449, 1987.
Giros et al., *Mol. Pharmacol.,* 42(3):383-390, 1992.
Giros et al., *Nature,* 379(6566):606-612, 1996.
Glassman et al., *J. Nerv. Ment. Dis.,* 173:573-576, 1985.
Hadrich et al., *J. Med. Chem.,* 42:3101-3108, 1999.
Hartzell, *J. Cell Biol.,* 86:6-20, 1980.
Hatfield and McGaugh, *Neurobiol. Learn. Mem.,* 71:232-239, 1999.
Herrera and Banner, *J. Neurocytol.,* 19:67-83, 1990.
Herrera et al., *J. Neurocytol.,* 19:85-99, 1990.
Ishikura et al., *Chem. Pharm. Bull.,* 11:4755-4763, 1985.
Iversen et al., *J. Pharmacol. Exp. Ther.,* 157:509-516, 1967.
Jacob et al., *Circulation,* 99:1706-1712, 1999.
Jones, *Prog. Brain Res.,* 88:381-394, 1991.
Kawarai et al., *Gene,* August 11, 195(1):11-8 1997.
Kitayama et al., *Neurosci. Lett.,* 312(2):108-112, 2001.
Koella, *Neuronal Serotonin,* Osborne et al. (eds.), 153-170, 1988.
Kuhar et al., *Trends Neurosci.,* 14(7):299-302, 1991.
Kuo, *J. Chinese Chem. Soc.* (Taipei, Taiwan), 25(3):131-139, 1978.
Le Bars, *Neuronal Serotonin,* Osborne and Hamin (eds), 171-229, 1988.
Lyapustina et al., *J. Photochem. Photobiol. A: Chem.,* 75(2): 119-123, 1993.
Maniatis, et al., Molecular Cloning, A Laboratory Manual, Cold Spring Harbor Press, Cold Spring Harbor, N.Y., 1988.
Masson et al., *Pharmacol. Rev.,* 51:439-464, 1999.
Naranjo et al., *Clin. Pharmacol. Ther.,* 41:266-274, 1987.
Neumeister et al., *Arch. Gen. Psychiatry,* 59(7):613-620, 2002.
Pacholczyk et al., *Nature,* March 28; 350(6316):350-4, 1991.
PCT Appln. WO 84/03564
Pelham, *Nature,* 389(6646):17, 19, 1997.
Pietruck and Ullrich, *Kidney Int.,* 47(6): 1647-1657, 1995.
Porzgen et al., *Biochem Biophys Res Commun.,* 227(2):642-643, 1996.
Prasad and Amara, *J. Neurosci.,* 21:7561-7567, 2001.
Ramamoorthy et al., *Biochemistry,* 32:1346-1353, 1993.
Ramamoorthy et al., *J. Biol. Chem.,* 273:2458-2466, 1998.
Ressler and Nemeroff, *Biol. Psychiatry,* 46:1219-1233, 1999.
Rohlicek and Ullrich, *Ren. Physiol. Biochem.,* 17(2):57-61, 1994.
Rudnick and Clark, *Biochim. Biophys. Acta,* 1144(3):249-63, 1993.
Samochowiec et al., *Neuropsychobiology,* 43(4):248-253, 2001.
Schloss, *Psychopharmacol.,* 12(2):115-121, 1998.
Silverstone et al., *Appetite,* 7:85-97, 1986.
Skrebitsky and Chepkova, *Rev. Neurosci.,* 9:243-264, 1998.
Sora et al., *Proc. Natl. Acad. Sci. USA,* 98(9):5300-5305, 2001.
Soubrie, In: *Neuronal Serotonin,* Osborne and Hamon (Eds.), 255-270, 1988.
Southwick et al., *Biol. Psychiatry,* 46:1192-1204, 1999.
Stober et al., *Lancet.,* 347(9011):1340-1341, 1996.
Tsai et al., *Neuropsychobiology,* 45(3):131-133, 2002.
Van Woert et al., *Monogr. Neural. Sci.,* 3:71-80, 1976.
Watanabe et al., *Jpn. Heart J.,* 22:977-985, 1981.
Zauhar et al., *Synthesis,* 6:703-706, 1995.

What is claimed is:

1. A method for measuring monoamine transport in a cell comprising:
 (a) providing a cell that expresses a monoamine transporter;
 (b) exposing the cell or the extract to a compound having the formula:

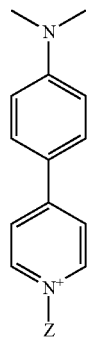

wherein the phenyl ring is unsubstituted or carries one, two, three or four substituents selected independently from $C_{1-12}$ alkyl, fluorinated alkyls, nitro, CN, SCN, OCN, amino, N-alkyl amino, N,N-dialkyl amino, F, Br, I, Cl, furyl, thiophenyl, pyridyl, piperidyl, phenyl, napthyl, OH, OR, SH, SR, $CONH_2$, CONHR, $SO_2NH_2$, $SO_2NHR$, COR, wherein R is $C_{1-12}$ alkyl;

wherein the pyridyl ring is unsubstituted or carries one, two three or four substituents selected independently from $C_{1-12}$ alkyl, fluorinated alkyls, nitro, CN, SCN, OCN, amino, N-alkyl amino, N,N-dialkyl amino, F, Br, I, Cl, furyl, thiophenyl, pyridyl, piperidyl, phenyl, napthyl, OH, OR, SH, SR, $CONH_2$, CONHR, $SO_2NH_2$, $SO_2NHR$, COR, wherein R is $C_{1-12}$ alkyl;

Z may be alkyl, aryl, or benzyl; and (c) measuring the transport of the compound, thereby measuring the transport of the monoamine in the cell.

2. The method of claim 1, wherein measuring transport further comprises measuring the kinetics of the monoamine transporter.

3. The method of claim 1, wherein measuring transport is in real time or as an endpoint assay following a defined time of fluorescence accumulation.

4. The method of claim 1, wherein measuring transport is by fluorescence microscopy or using a fluorescent plate reader.

5. The method of claim 1, wherein the time resolution of measuring transport is 5 hours to 50 milliseconds.

6. The method of claim 1, wherein the cell is a neuronal or glial cell.

7. The method of claim 1, wherein the cell is a blood platelet or lymphocyte.

8. The method of claim 1, wherein the cell is a placental cell.

9. The method of claim 1, wherein the cell is a trophoblast.

10. The method of claim 1, wherein the monoamine transporter is an endogenously expressed transporter.

11. The method of claim 1, wherein the monoamine transporter is an exogenously expressed transporter.

12. The method of claim 1, wherein the monoamine neurotransmitter transporter is a norepinephrine transporter.

13. The method of claim 1, wherein the monoamine neurotransmitter transporter is an epinephrine transporter.

14. The method of claim 1, wherein the monoamine neurotransmitter transporter is a dopamine transporter.

15. The method of claim 1, wherein the monoamine neurotransmitter transporter is a serotonin transporter.

16. The method of claim 1, wherein both the phenyl ring and the pyridyl ring are unsubstituted, and Z is nPr.

17. The method of claim 1, wherein both the phenyl ring and the pyridyl ring are unsubstituted, and Z is ethyl.

18. The method of claim 1, wherein both the phenyl ring and the pyridyl ring are unsubstituted, and Z is methyl.

19. The method of claim 1, wherein the pyridyl ring is unsubstituted, the phenyl ring comprises a fluorine substituent and Z is methyl.

20. The method of claim 1, wherein the pyridyl ring is unsubstituted, the phenyl ring comprises a methyl substituent and Z is methyl.

21. A method of screening for agents that can modulate the activity of a monoamine transporter comprising:

(a) providing a cell that expresses a monoamine transporter;

(b) exposing said cell to an agent that is a candidate monoamine transporter modulator;

(c) exposing the cell a compound having the formula:

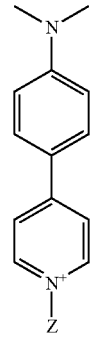

wherein the phenyl ring is unsubstituted or carries one, two, three or four substituents independently selected from $C_{1-12}$ alkyl, fluorinated alkyls, nitro, CN, SCN, OCN, amino, N-alkyl amino, N,N-dialkyl amino, F, Br, I, Cl, furyl, thiophenyl, pyridyl, piperidyl, phenyl, napthyl, OH, OR, SH, SR, $CONH_2$, CONHR, $SO_2NH_2$, $SO_2NHR$, COR, wherein R is $C_{1-12}$ alkyl;

wherein the pyridyl ring is unsubstituted or carries one, two three or four more substituents selected independently from $C_{1-12}$ alkyl, fluorinated alkyls, nitro, CN, SCN, OCN, amino, N-alkyl amino, N,N-dialkyl amino, F, Br, I, Cl, furyl, thiophenyl, pyridyl, piperidyl, phenyl, napthyl, OH, OR, SH, SR, $CONH_2$, CONHR, $SO_2NH_2$, $SO_2NHR$, COR, wherein R is $C_{1-12}$ alkyl;

Z may be alkyl, aryl, or benzyl;

(d) measuring the transport of the compound; and (e) comparing the transport of the compound in said cell to the transport of the compound in a cell that has not been exposed to the agent, thereby determining if the agent is a modulator of activity of said monoamine transporter.

22. The method of claim 21, further comprising the use of a fluorescent plate reader to provide high-throughput screening of agents.

23. The method of claim 21, wherein the monoamine transporter is a norepinephrine transporter.

24. The method of claim 21, wherein said method is an in vivo method.

25. The method of claim 21, wherein said method is an in vitro method.

26. The method of claim 21, wherein the cell is a neuronal or glial cell, a blood platelet or lymphocyte, a placental cell, or a trophoblast.

27. The method of claim 21, wherein the monoamine transporter is an epinephrine transporter.

28. The method of claim 21, wherein the monoamine transporter is a dopamine transporter.

29. The method of claim 21, wherein the monoamine transporter is a serotonin transporter.

30. The method of claim 21, wherein both the phenyl ring and the pyridyl ring are unsubstituted, and Z is nPr.

31. The method of claim 21, wherein both the phenyl ring and the pyridyl ring are unsubstituted, and Z is ethyl.

32. The method of claim 21, wherein both the phenyl ring and the pyridyl ring are unsubstituted, and Z is methyl.

33. The method of claim 21, wherein the pyridyl ring is unsubstituted, the phenyl ring comprises a fluorine substituent and Z is methyl.

34. The method of claim 21, wherein the pyridyl ring is unsubstituted, the phenyl ring comprises a methyl substituent and Z is methyl.

* * * * *

UNITED STATES PATENT AND TRADEMARK OFFICE
CERTIFICATE OF CORRECTION

PATENT NO. : 7,947,255 B2  Page 1 of 1
APPLICATION NO. : 11/832905
DATED : May 24, 2011
INVENTOR(S) : Randy D. Blakely et al.

It is certified that error appears in the above-identified patent and that said Letters Patent is hereby corrected as shown below:

In column 1, lines 8-10, delete paragraph and insert
--This invention was made with government support under grant numbers R01EB03728-03 and R01DA07390 RB awarded by the National Institutes of Health. The government has certain rights in the invention.-- therefor.

Signed and Sealed this
Twenty-third Day of August, 2011

David J. Kappos
*Director of the United States Patent and Trademark Office*